United States Patent [19]

Kenjo et al.

[11] Patent Number: 4,731,192

[45] Date of Patent: Mar. 15, 1988

[54] CLEANING SYSTEM FOR CONTACT LENSES AND PROCESS FOR CLEANING THE SAME

[75] Inventors: Hideki Kenjo, Otsu; Teruo Jyono, Shiga, both of Japan

[73] Assignee: Toray Industries, Inc., Otsu, Japan

[21] Appl. No.: 841,828

[22] Filed: Mar. 20, 1986

[30] Foreign Application Priority Data

Mar. 26, 1985 [JP] Japan ................................ 60-61599

[51] Int. Cl.$^4$ ............................................. C11D 7/54
[52] U.S. Cl. .................................. 252/95; 206/524.1; 252/90; 252/94; 424/149; 514/839; 514/840
[58] Field of Search ............................ 252/94, 90, 95; 424/149; 514/839, 840; 206/524.1

[56] References Cited

U.S. PATENT DOCUMENTS 3,873,696 3/1975 Randeri et al. .................... 252/94

FOREIGN PATENT DOCUMENTS 1861683 2/1983 Japan .
196723 10/1985 Japan .
85/04107 9/1985 World Int. Prop. O. .

OTHER PUBLICATIONS

GAF Corporation, Technical Bulletin 7543-113, "Polyvinylpyrrolidone, Physical, Chemical, Physiological and Functional Properties", 1964.

Primary Examiner—Paul Lieberman
Assistant Examiner—Linda D. Skaling
Attorney, Agent, or Firm—Wegner & Bretschneider

[57] ABSTRACT

A contact lens cleaning system, process and kit includes an aqueous chlorite solution and a solid component including an agent for accelerating decomposition of chlorite and an oxygen consumption agent. The chlorite decomposes to form free oxygen which removes impurities from a lens to be cleaned. The oxygen consuming agent prevents excess free oxygen from attacking the lens after the impurities have been removed.

22 Claims, 1 Drawing Figure

CLEANING SYSTEM FOR CONTACT LENSES AND PROCESS FOR CLEANING THE SAME

BACKGROUND OF THE INVENTION

1. Field of the Invention

The present invention relates to a cleaning agent for soft and hard contact lenses (hereinafter referred to as CL) and a process for using the same.

2. Description of the Prior Art

It has been known to clean CL by removing oils, fats and dirts from the surface of CL with a cleaning solution containing, for example, an acid, a chlorite and a surfactant (Japanese patent Laid-Open Nos. 18616/1983 and 18617/1983). It has also been known that substances such as proteins which cannot be removed with a surfactant or the like are removed by decomposing them with protease.

However, the cleaning solutions used heretofore are those of a two-pack type. In using these solutions, a troublesome operation is required of the users, namely, the two liquids must be measured separately and then placed in a cleaning vessel. Further, containers of a large volume are necessitated for the two liquids. This is inconvenient for a traveler making a trip for a long period of time.

SUMMARY OF THE INVENTION

After intensive investigations made for the purpose of overcoming the defects of the conventional cleaning solutions for contact lenses and processes for cleaning them, the inventors have developed a cleaning agent of a two-pack type in which one pack comprises an easily measurable solid and a process for cleaning contact lenses. The cleaning agent can be kept compact as a whole and used easily and conveniently for cleaning contact lenses.

A first embodiment of this invention is directed to a cleaning system for contact lenses, comprising:

(a) a chlorite salt in aqueous solution, capable of decomposition to form free oxygen for removing impurities from a contact lens.

(b) a solid component, comprising:

an agent for accelerating the decomposition of the chlorite to form free oxygen, selected from the group consisting of acids, organic acid salts, ion exchange resins, reducing agents and sugars; and oxygen-consuming agent for consuming excess free oxygen from the decomposition of the chlorite after impurities have been removed from a contact lens being cleaned.

A second embodiment of the invention provides a process for cleaning contact lenses, comprising placing a lens to be cleaned, and a cleaning system comprising:

(a) a chlorite salt in aqueous solution, capable of decomposition to form free oxygen for removing impurities from a contact lens.

(b) a solid component, comprising:

an agent for accelerating the decomposition of the chlorite to form free oxygen, selected from the group consisting of acids, organic acid salts, ion exchange resins, reducing agents and sugars; and oxygen-consuming agent for consuming excess free oxygen from the decomposition of the chlorite after impurities have been removed from a contact lens being cleaned in a vessel.

A third embodiment of the invention provides a cleaning system for contact lenses, comprising:

(a) a chlorite salt in aqueous solution, capable of decomposition to form free oxygen for removing impurities from a contact lens;

(b) a solid component, comprising:

an acid for accelerating decomposition of the chlorite to form free oxygen;

a sugar for consuming excess free oxygen from the decomposition from the chlorite after impurities are removed from the lens; and a decomposition inhibitor for the acid.

A further aspect of the invention is directed to a process for cleaning contact lenses, comprising placing a lens to be cleaned and a cleaning system comprising (a) a chlorite salt in aqueous solution, capable of decomposition to form free oxygen for removing impurities from a contact lens;

(b) a solid component, comprising:

an acid for accelerating decomposition of the chlorite to form free oxygen;

a sugar for consuming excess free oxygen from the decomposition from the chlorite after impurities are removed from the lens; and a decomposition inhibitor for the acid in a vessel.

Yet another aspect of the invention provides a contact lens cleaning kit, comprising:

(a) a container with a chlorite salt in aqueous solution, capable of decomposition to form free oxygen for removing impurities from a contact lens; and (b) a plurality of packages containing pre-measured amounts of:

an agent for accelerating the decomposition of the chlorite to form free oxygen, selected from the group consisting of acids, organic acid salts, ion exchange resins, reducing agents and sugars; and an oxygen-consuming agent for consuming excess free oxygen from the decomposition of the chlorite after impurities have been removed from a contact lens being cleaned.

DETAILED DESCRIPTION

Figure 1:
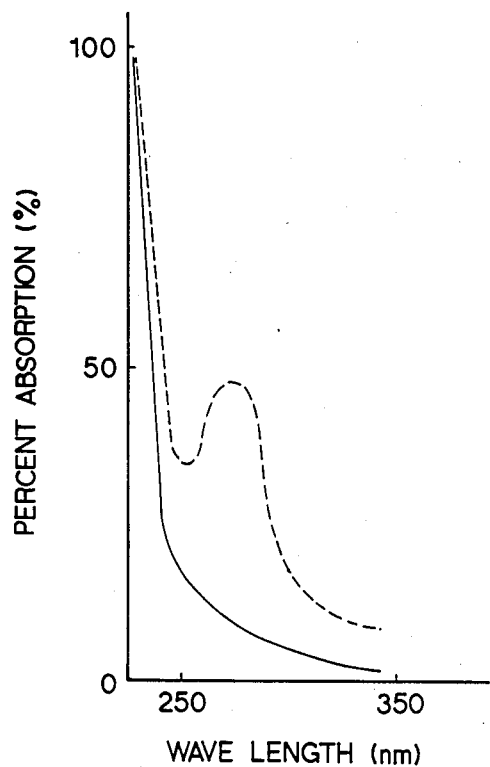
FIG. 1 is a chart showing UV spectra of a lens, wherein the dotted line shows the UV spectrum of the stained lens before cleaning and the solid line shows that of the lens treated with the cleaning agent of the present invention.

Examples of the chlorites contained in the liquid A include sodium and potassium chlorites. Among them, sodium chlorite is particularly preferred, since it effectively decomposes excretions from the living body which are deposited on the contact lenses with minimal effect on the lenses. Specifically, it is believed that the chlorite ion decomposes to release free oxygen, which attacks the impurities on the lens.

The concentration of the chlorite in the cleaning solution is in the range of about 0.0001 to 5% by weight, preferably 0.0005 to 0.5%. For storage stability, a pH in the range of about 6-8 is preferred for the chlorite solution.

In the present invention, the component B should be in a solid form so as to facilitate the handling thereof. The form of the solid component B is not particularly limited and it may be in the form of tablet, powder or pellet (including granule). Among them, a pellet or powder is particularly effective. It is preferred to pack a batch of the component in a bag.

The component B must comprise at least one member selected from the group consisting of acids, organic acid salts, ion exchange resins, reducing agents and sugars.

These agents act as catalysts for accelerating the decomposition of the chlorite contained in the component A. The agents may function by releasing hydrogen ions, which leads to accelerated decomposition of the chlorite to from free oxygen.

The sugar may be any one having the above-mentioned function and it may be selected from monosaccharides and polysaccharides. A typical example of the sugar is glucose.

The acid may be any one as long as it provides the function required in the present invention. Preferred examples of the acids include organic acids such as adipic, stearic, sebacic, oxalic, itaconic, edetic, ascorbic; and inorganic acids such as hydrochloric and sulfuric acids. It is more preferred to use tartaric and/or citric acid. Acids which are normally liquid can be used in a solid form through absorption on a substrate such as alumina or encapsulation in a suitable acid resistant polymer. In the case of absorption, the chlorite solution itself will release the acid, while some mechanical force may be necessary in the case of encapsulation. The ion exchange resin is preferably a cation exchange resin. The ion exchange resin functions as the acid does, and has the advantage of being in solid form, and thus easily removed after the cleaning is finished. The organic acid salt is at least one of sodium hydrogentartrate and sodium dihydrogencitrate. Polyfunctional acid salts are preferred because of the removable acid functions in such salts, which provide the salts with the same properties as an acid with respect to the present invention. Also, such salts often are conveniently available in solid form. The reducing agent is preferably sodium hydrogensulfite.

These compounds accelerate the decomposition of the chlorite.

The pH value of the cleaning solution may be selected suitably so far as the purpose of the present invention is not damaged. It is, for example, in the range of 2 to 8, preferably 3 to 6.

The cleaning agent of the present invention also may contain known additives which do not interfere with the invention, such as: sodium monohydrogenphosphate, urea, boric acid, sodium borate, and edetic acid salts as well as surfactants. These function as preservatives, protein denaturants, etc.

The component B may comprise at least one sugar, an acid and a decomposition inhibitor for the acid.

The combination of the sugar with the acid acts as a catalyst for accelerating the decomposition of the chlorite.

The sugar may be any one having the above-mentioned function and it may be selected from among monosaccharides and polysaccharides. Examples of the sugars include glucose, sucrose and fructose. Among them, glucose is particularly preferred. The sugar releases hydrogen ions under the influence of the acid, thus contributing to the decomposition of the chlorite. Furthermore, the sugar functions to consume excess free oxygen remaining after the decomposition of impurities so that the excess free oxygen is not available to deteriorate the lens. This latter function of the sugar can be accomplished using other materials so long as the free oxygen attacks the lens impurities before being consumed. An example of a suitable substitute material is a polymer such as polyvinylpyrrolidone.

The acid may be any one so far as it has the function intended in the present invention. Preferred examples of the acids include organic acids such as tartaric, citric, lactic, malic and gluconic acids; and inorganic acids such as hydrochloric and sulfuric acids. It is more preferred to use tartaric and/or citric acid.

A preferred combination of the sugar with the acid comprises citric acid and glucose, since it exhibits an excellent cleaning effect without damaging the physical properties of the lenses. They may be used either alone or in the form of a mixture of two or more of them. The sugar alone will provide some acceleration of the chlorite decomposition, but the efficiency is increased by also using acid.

The present invention is characterized in that a decomposition inhibitor for the acid is contained in the component B. When a solid mixture of the acid and the sugar is stored for a long period of time, the acid frequently is decomposed, which lowers the cleaning power unfavorably. Though this defect can be prevented by granulating the acid and the sugar separately from each other, this technique is troublesome. According to the present invention, this defect can be overcome by using the decomposition inhibitor. Though any compound having such an effect can be used as said inhibitor, polyvinyl compounds, particularly polyvinylpyrrolidone, are preferred. The molecular weight of the polyvinylpyrrolidone is not particularly limited and it ranges from several thousands to several millions.

The cleaning agent of the present invention can be used for cleaning conventional contact lenses to exhibit not only a protein-removing effect but also a decolorizing effect within a short treatment time.

A preferred embodiment of the process for cleaning contact lenses with the cleaning agent of the present invention is as follows: a given amount (for example, a batch packed in a bag) of the solid component B is placed in a vessel together with the lenses and then a given amount (for example, corresponding to a scale mark of the cleaning vessel) of the liquid A is added thereto to clean the lenses.

The temperature of the cleaning solution may be selected suitably. More particularly, it may be room temperature or from around a boiling point to 120° C. The lower the temperature, the longer the treatment time and, on the contrary, the higher the former, the shorter the latter.

The contact lenses thus treated are preferably left to cool to room temperature in the cleaning solution and then washed with water. If necessary, any remaining chlorite is decomposed with sodium thiosulfate or sodium hydrogensulfite. The lenses are then immersed in a physiological saline and used again.

The contact lenses which can be treated by the above-mentioned cleaning process include, for example, highly hydrous, soft contact lenses comprising mainly polyvinylpyrrolidone and less hydrous soft contact lenses comprising mainly polyhydroxyethyl methacrylate. Further, hard contact lenses having a polysiloxane bond, oxygen-permeable contact lenses having both siloxane and urethane bonds, etc. may also be treated as a matter of course. Thus, the kinds of the contact lenses which can be treated according to the present invention are not limited.

The cleaning agent of the present invention in which one of the components is in solid form has advantages in that it can be weighed easily at the time of the use and it can be stored compact as a whole. The present invention has advantageous effects in that it provides a convenient cleaning agent and process for the users.

Another effect of the invention is that the cleaning agent can be stored for a long period of time and that the cleaning can be effected in a consistent manner.

The cleaning agent can be sold in a kit form containing a number of pre-measured units of the solid component (preferably individual packages), a container with chlorite solution and instructions for use. Optionally, the kit can include a cleaning container for lenses, marked to indicate the appropriate level for chlorite solution addition.

EXAMPLE 1

12 g of polyvinylpyrrolidone having an average molecular weight of about 360,000 was added to a mixture of 80 g of D-(+)-glucose and 8 g of L-(+)-tartaric acid. 5 g of pure water was added thereto and the mixture was stirred well and granulated. The granules were dried at 60° C. for 1 h and then heat-treated at 40° C. for 80 h. The tartaric acid content was measured according to ion chromatography before and after the heat treatment to reveal that they were 7.78% and 7.89%, respectively. The difference between them was thus insignificant. This fact suggests that the product has a good storage stability. 4 ml of 100 ppm aqueous sodium chlorite solution was added to 0.1 g of the granules. A used, stained soft contact lens was immersed therein and boiled at 100° C. for 15 min. Then, it was left to cool to room temperature. The lens was washed with running pure water for 5 min and its UV spectrum was examined to evaluate the cleaning effects. The results are shown in Table 1. Satisfactory cleaning effects were obtained.

The accompanying FIG. 1 is a chart showing UV spectra of the lens in which the dotted line shows the UV spectrum of the lens before cleaning and the solid line shows that after cleaning. The peak in the dotted line shows the presence of contaminant.

EXAMPLE 2

Cleaning solutions Nos. 2 to 4 as shown in Table 1 were prepared by granulation and pulverization effected in the same manner as in Example 1. A used, stained contact lens was immersed in each solution and boiled at 100° C. for 15 min or left to stand at room temperature for 16 h. The lens was washed with running water for 5 min and the UV spectrum thereof was examined to evaluate the cleaning effects. The results are shown in Table 1.

The cleaning of the effect which the degree of staining of the lens placed on the colorimetric dish was ranked visually as follows:

| Rank | Degree of staining of the lens |
|---|---|
| 4 | The staining and discoloration were serious |
| 3 | The staining and discoloration were moderate |
| 2 | The staining and discoloration were slight |
| 1 | The staining and discoloration were negligible |

TABLE 1

| (Composition of the solution) | Cleaning solution No. | | | |
|---|---|---|---|---|
| | 1 | 2 | 3 | 4 |
| Component A | | | | |
| Sodium chlorite | 0.01% | 0.01% | 0.01% | 0.01% |
| Pure water | 99.99 | 99.99 | 99.99 | 99.99 |
| Amount of component A | 4 g | 4 g | 4 g | 4 g |
| Component B | | | | |
| Glucose | 80% | 80% | 80% | — |
| Fructose | — | — | — | 100% |
| Tartaric acid | 8% | 8% | — | — |
| Citric acid | — | — | 20% | — |
| Polyvinylpyrrolidone | 12% | 12% | — | — |
| (Average molecular weight of polyvinylpyrrolidone) | 360,000 | 25,000 | | |
| Amount of component B | 0.1 g | 0.1 g | 0.1 g | 0.2 g |
| (Treatment conditions) | | | | |
| Temperature | 100° C. | room temp. | 100° C. | 100° C. |
| Time | 15 min | 16 h | 15 min | 15 min |
| (Cleaning effect) | 1 | 2 | 1 | 2 |

EXAMPLE 3

12 g of polyvinylpyrrolidone having an average molecular weight of about 25,000 was added to a mixture of 80 g of D-(+)-glucose and 8 g of L-(+)-tartaric acid and the mixture was stirred thoroughly. 4 ml of 100 ppm sodium chlorite solution was added to 0.1 g of the obtained powder. Further, 1 ml of an aqueous urea solution prepared according to a formulation shown below was added to the mixture. A used, stained contact lens was immersed therein and left to stand at room temperature for 16 h. Thereafter, the lens was taken out and washed with running pure water for 5 min. The cleaning effect was determined by a visual method wherein the lens placed in a colorimetric dish was observed before and after the cleaning. The results are shown in Table 2. Excellent cleaning effects were obtained.

| Aqueous urea solution: | |
|---|---|
| polyoxyethylene sorbitan monolaurate | 0.3% |
| polyoxyethylene/polyoxypropylene | 0.3% |
| sodium carboxymethylcellulose | 0.02% |
| potassium sorbate | 0.005% |
| urea | 1.0% |
| pure water | the balance |

TABLE 2

| (Composition of the solution) | Cleaning solution No. | | | | |
|---|---|---|---|---|---|
| | 5 | 6 | 7 | 8 | 9 |
| Component A | | | | | |
| Sodium chlorite (%) | 0.01 | 0.01 | 0.01 | 0.01 | 0.01 |
| Pure water (%) | 99.99 | 99.99 | 99.99 | 99.99 | 99.99 |
| Amount of component A (g) | 4 | 4 | 4 | 4 | 4 |
| Component B | | | | | |
| Glucose (%) | 80 | 80 | 80 | — | 80 |
| Tartaric acid (%) | 8 | 8 | 20 | 20 | — |
| Polyvinylpyrrolidone (%) | 12 | 12 | — | — | — |
| (Average molecular weight of polyvinylpyrrolidone) (× 10,000) | 2.5 | 2.5 | | | |
| Amount of component B (g) | 0.01 | 0.01 | 0.01 | 0.01 | — |

TABLE 2-continued

| (Composition of the solution) | Cleaning solution No. | | | | |
|---|---|---|---|---|---|
| | 5 | 6 | 7 | 8 | 9 |
| Component C | | | | | |
| Polyoxyethylene sorbitan monolaurate (%) | — | 0.3 | — | 0.6 | 0.3 |
| Polyoxyethylene/polyoxypropylene block polymer (%) | — | 0.3 | — | 0.6 | 0.3 |
| Sodium carboxymethylcellulose (%) | — | 0.02 | — | 0.04 | 0.02 |
| Potassium sorbate (%) | — | 0.05 | — | 0.01 | 0.005 |
| Urea (%) | — | 1.0 | 2.0 | — | 1.0 |
| Pure water (%) | — | 98.375 | 98.0 | 98.75 | 98.375 |
| Amount of component A (g) | — | 1 | 1 | 1 | 1 |
| (Treatment conditions) | | | | | |
| Temperature | room temp | room temp | room temp | room temp | room temp |
| Time (h) | 16 | 16 | 16 | 16 | 16 |
| (Cleaning effect) | | | | | |
| Before cleaning | 4 | 4 | 4 | 4 | 4 |
| After cleaning | 3 | 2 | 2 | 2 | 3 |

EXAMPLE 4

Cleaning solutions Nos. 7 to 9 as shown in Table 2 were prepared by using the same aqueous urea solution as in Example 3 as it was or after modifying the composition thereof. A used, stained contact lens was immersed in each solution and left to stand at room temperature for 16 h. The lens was washed with running water for 5 min and the cleaning effect was evaluated using the colorimetric dish. The results are shown in Table 2. The cleaning effect was improved remarkably by the addition of the aqueous urea solution.

COMPARATIVE EXAMPLE 1

A granular component B was prepared in the same manner as in Example 1 except that the polyvinylpyrrolidone used as the decomposition inhibitor for the acid was not added. More particularly, 98 g of D-(+)glucose was mixed with 2 g of L-(+)-tartaric acid. 17 g of pure water was added to the mixture and the obtained mixture was granulated. The granules were dried at 60° C. for 1 h and then heat-treated at 40° C. for 80 h. The tartaric acid content of the heat-treated granules was analyzed according to ion chromatography to reveal that it was reduced by about 16% from 1.97% to 1.65% by the heat treatment. The product had thus a poor stability. The decomposition products of the acid may not be safe to humans.

When the obtained cleaning agent was used for cleaning a contact lens, only a poor cleaning effect was obtained.

EXAMPLE 5

0.003 g of crystalline citric acid was added to 3 g of 0.01% aqueous sodium chlorite solution. Then, a used, stained soft contact lens was immersed therein and boiled at 100° C. for 30 min. Then, it was left to cool to room temperature. The lens was washed with running pure water for 5 min and its UV spectrum was examined to evaluate the cleaning effects. The results are shown No. 10 in Table 3. Satisfactory cleaning effects were obtained.

EXAMPLE 6

Cleaning solution Nos. 11 to 15 as shown in Table 3 were prepared in the same manner as in Example 5. A used, stained contact lens was immersed in each solution and boiled at 100° C. for 10 to 30 min or left to stand at room temperature for 16 h. The lens was washed with running pure water for 5 min and the UV spectrum thereof was examined to evaluate the cleaning effects. The results are shown in Table 3.

TABLE 3

| (Composition of the solution) | Cleaning solution No. | | | | | |
|---|---|---|---|---|---|---|
| | 10 | 11 | 12 | 13 | 14 | 15 |
| Component A | | | | | | |
| Sodium chlorite (%) | 0.01 | 0.01 | 0.02 | 0.02 | 0.02 | 0.02 |
| Pure water | 99.99 | 99.99 | 99.98 | 99.98 | 99.98 | 99.98 |
| Amount of component A (g) | 3 | 3 | 3 | 3 | 3 | 3 |
| Component B | | | | | | |
| Citric acid (%) | 100 | | | | | |
| Tartaric acid (%) | | 100 | | | | |
| L-Aspartic acid (%) | | | 100 | | | |
| Oxalic acid (%) | | | | 100 | | |
| Ascorbic acid (%) | | | | | 100 | |
| Itaconic acid (%) | | | | | | 100 |
| Amount of component B (g) | 0.003 | 0.03 | 0.01 | 0.01 | 0.01 | 0.01 |
| (Treatment conditions) | | | | | | |
| Temperature (°C.) | 100 | room temp. | 100 | 100 | 100 | 100 |
| Time (min.) | 30 | (16 hr) | 10 | 10 | 10 | 10 |
| (Cleaning effect) | 1 | 1 | 2 | 1 | 2 | 1 |

EXAMPLE 7

Cleaning solution Nos. 16 to 19 as shown in Table 4 were prepared by using a granulated organic acid salt, reducing agent or reducing sugar in the same manner as in Example 5. A used, stained contact lens was immersed therein and boiled at 100° C. for 10 to 60 min. Thereafter, the lens was washed with running pure water for 5 min. The cleaning effect was determined from the UV spectrum of the treated lens. The results are shown in Table 4.

TABLE 4

| (Composition of the solution) | Cleaning solution No. | | | |
|---|---|---|---|---|
| | 16 | 17 | 19 | 20 |
| Component A | | | | |
| Sodium chlorite (%) | 0.02 | 0.02 | 0.02 | 0.02 |
| Pure water (%) | 99.98 | 99.98 | 99.98 | 99.98 |
| Amount of component A (g) | 3 | 3 | 3 | 3 |
| Component B | | | | |
| Sodium hydrogentartrate (%) | 100 | | | |
| Sodium dihydrogencitrate (%) | | 100 | | |
| Glucose (%) | | | 100 | |
| Sodium hydrogensulfite | | | | 100 |
| Amount of component B (g) | 0.01 | 0.01 | 0.01 | 0.01 |
| (Treatment conditions) | | | | |
| Temperature (°C.) | 100 | 100 | 100 | 100 |
| Time (min) | 10 | 10 | 60 | 10 |
| (Cleaning effect) | 2 | 2 | 1 | 1 |

EXAMPLE 8

0.01 g of Amberlyst #5 (an ion exchange resin of Rohm Haas) was added to 3 g of 0.02 to 0.05% aqueous sodium chlorite solution. Cleaning solutions No. 20 or 21 as shown in Table 5 was added thereto. A used, stained lens was immersed therein. After boiling at 100° C. for 10 min or leaving to stand at room temperature for 16 h, the lens was taken out and washed in running pure water. The UV spectrum of the lens was examined before and after the treatment to evaluate the cleaning effect. The results are shown in Table 5.

TABLE 5

| (Composition of the solution) | Cleaning Solution No. | |
|---|---|---|
| | 20 | 21 |
| Component A | | |
| Sodium chlorite (%) | 0.02 | 0.05 |
| Pure water (%) | 99.98 | 99.95 |
| Amount of component A (g) | 3 | 3 |
| Component B | | |
| Amberlyst-15 | 100 | 100 |
| Amount of component B (g) | 0.01 | 0.01 |
| (Treatment conditions) | | |
| Temperature (°C.) | 100 | room temp. |
| Time | 10 min | 16 hr |
| (Cleaning effect) | 2 | 1 |

What is claimed is:

1. A cleaning system for contact lenses, comprising:
   (a) a chlorite salt in aqueous solution, capable of decomposition to form free oxygen for removing impurities from a contact lens; and
   (b) a solid component, comprising:
      an agent for accelerating the decomposition of the chlorite to form free oxygen, comprising at least one member selecting from the group consisting of acids and organic acid salts;
      an oxygen-consuming agent for consuming excess free oxygen from the decomposition of the chlorite after impurities have been removed from a contact lens being cleaned; and
      polyvinylpyrrolidone as a decomposition inhibitor for said agent for accelerating the decomposition of the chlorite.

2. The system of claim 1, wherein the solid component is in the form of a pellet or power.

3. The system of claim 1, wherein the agent for accelerating the decomposition is at least one organic acid.

4. The system of claim 1, wherein the agent for accelerating the decomposition is a cation exchange resin.

5. The system of claim 1, wherein the agent for accelerating the decomposition further comprises at least one member selected from the group consisting of adipic, stearic, sebacic, oxalic, itaconic, edetic, ascorbic, alginic, aspartic, sorbic, tartaric and citric acids.

6. The cleaning agent of claim 1, wherein the agent for accelerating the decomposition is at least one member selected from the group consisting of sodium hydrogentartrate and sodium dihydrogencitrate.

7. The system of claim 1, wherein the agent for accelerating the decomposition further comprises sodium hydrogensulfite.

8. The system of claim 1, wherein the agent for accelerating the decomposition further comprises glucose.

9. A process for cleaning contact lenses, comprising placing a lens to be cleaned, and a cleaning system comprising:
   (a) a chlorite salt in aqueous solution, capable of decomposition to form free oxygen for removing impurities from a contact lens; and
   (b) a solid component, comprising:
      an agent for accelerating the decomposition of the chlorite to form free oxygen, comprising at least one member selected from the group consisting of acids and organic acid salts;
      an oxygen-consuming agent for consuming excess free oxygen from the decomposition of the chlorite after impurities have been removed from a contact lens being cleaned; and
      polyvinylpyrrolidone as a decomposition inhibitor for the agent for accelerating the decomposition of the chlorite in a vessel.

10. A cleaning system for contact lenses, comprising:
    (a) a chlorite salt in aqueous solution, capable of decomposition to form free oxygen for removing impurities from a contact lens; and
    (b) a solid component, comprising:
       an acid for accelerating decomposition of the chlorite to form free oxygen;
       a sugar for consuming excess free oxygen from the decomposition of the chlorite after impurities are removed from the lens; and
       polyvinylpyrrolidone as a decomposition inhibitor for the acid.

11. The system of claim 10, wherein the solid component is in the form of a pellet or powder.

12. The system of claim 10, wherein the sugar is at least one member selected from the group consisting of glucose, sucrose and fructose.

13. The system of claim 10, wherein the acid is at least one member selected from the group consisting of adipic, stearic, sebacic, oxalic, itaconic, edetic, ascorbic, alginic, aspartic, sorbic, tartaric and citric acids.

14. A process for cleaning contact lenses, comprising placing a lens to be cleaned and a cleaning system comprising:
    (a) a chlorite salt in aqueous solution, capable of decomposition to form free oxygen for removing impurities from a contact lens; and (b) a solid component, comprising:
   an acid for accelerating decomposition of the chlorite to form free oxygen;
   a sugar for consuming excess free oxygen from the decomposition of the chlorite after impurities are removed from the lens; and
   polyvinylpyrrolidone as a decomposition inhibitor for the acid in a vessel.

15. A contact lens cleaning kit, comprising:
(a) a container with a chlorite salt in aqueous solution, capable of decomposition to form free oxygen for removing impurities from a contact lens;
(b) a plurality of packages containing pre-measured amounts of:
   an agent for accelerating the decomposition of the chlorite to form free oxygen, comprising at least one member selected from the group consisiting of acids and organic acid salts
   an oxygen-consuming agent for consumming excess free oxygen from the decomposition of the chlorite after impurities have been removed from a contact lens being cleaned; and
   polyvinylpyrrolidone as a decomposition inhibitor for the agent for accelerating the decomposition of the chlorite; and
(c) instructions for using the kit to clean a contact lens.

16. The kit of claim 15, wherein the agent for accelerating decomposition is an acid and the oxygen-consuming agent is a sugar.

17. The kit of claim 16, wherein the acid is selected from the group consisting of adipic, stearic, sebacic, oxalic, itaconic, edetic, ascorbic, alginic, aspartic, sorbic, tartaric and citric acids.

18. The kit of claim 16, wherein the sugar is at least one member selected from the group consisting of glucose, sucrose and fructose.

19. The kit of claim 14, further comprising a cleaning vessel for accepting a contact lens to be cleaned.

20. The cleaning system of claim 1, wherein the agent for accelerating the decomposition of the chlorite further comprises at least one member selected from the group consisted of ion exchange resins, reducing agents and sugars.

21. The process of claim 9, wherein the agent for accelerating the decomposition of the chlorite further comprises at least one member selected from the group consisting of ion exchange resins, reducing agents and sugars.

22. The kit of claim 15, wherein the agent for accelerating the decomposition of the chlorite further comprises at least one member selected from the group consisting of ion exchange resins, reducing agents and sugars.

* * * * *